United States Patent
Wegner et al.

(10) Patent No.: US 6,407,291 B1
(45) Date of Patent: Jun. 18, 2002

(54) PREPARATION OF 1,1,4,4-TETRAMETHOXY-2-BUTENE

(75) Inventors: Christoph Wegner, Kirchheim; Joachim Paust, Neuhofen; Hansgeorg Ernst, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/670,026

(22) Filed: Sep. 26, 2000

(30) Foreign Application Priority Data

Sep. 30, 1999 (DE) .......................... 199 46 816

(51) Int. Cl.$^7$ ............................ C07C 43/303
(52) U.S. Cl. ...................... 568/598; 568/603
(58) Field of Search ................. 568/598, 603

(56) References Cited

U.S. PATENT DOCUMENTS 2,768,976 A 10/1956 Weldlich et al. ............. 260/615
5,338,888 A * 8/1994 Paust et al. .................. 568/596

OTHER PUBLICATIONS

Makin et al., The Chemistry of Unsaturated ethers, . . . , pp. 1082–1087, translated from Zh. Obshch. Khim., vol. 32, No. 4, Apr. 1962, pp. 1104–1111.*

Cox et al., "Synthetic Studies on Electron Transport Inhibitors. Part 2. Approaches to the Synthesis of Myxalanide D" J. Chem. Soc. Perkin Trans.(1991) pp. 1907–1911.

Likhosherstov "Reactions of Alkoxyfuran and Alkoxypyrans with Alcohols in Acid Medium"Jour. Org. Chem. (1983) pp. 1176–1178.

Clauson et al. "Note on the Preparation of Acetals of Alkoxysuccinaldehydes" Acta Chemica Scandinavica (1955) pp. 111–116.

Gillespie "Fluorosulfuric Acid and Related Superacid Media" Acc. Chem. Res. vol. 1 (1968) pp. 202–209.

Gillespie et al. "Superacid Systems" Adv. Phys. Org. Chem. vol. 9 (1972) pp. 1–24.

Arata "Preparation of superacids by metal oxides for reactions of butanes and pentanes" Applied Catalysts A: General 146 (1996) pp. 3–32.

Figueras "Pillared Clays as Catalysts" Catal. Rev. Sci. Eng. vol. 30 (1988) pp. 457–499.

Jones "The Structure and Properties of Pillared Clays" Catalysis Today vol. 2 (1988) pp. 357–367.

* cited by examiner

*Primary Examiner*—Rosalynd Keys
(74) *Attorney, Agent, or Firm*—Keil & Weinkauf

(57) ABSTRACT

A process for the preparation of 1,1,4,4-tetramethoxy-2-butene by reacting 2,5-dimethoxydihydrofuran with methanol in the presence of acids comprises carrying out the reaction in the presence of solid catalysts having acidic centers.

7 Claims, No Drawings

PREPARATION OF 1,1,4,4-TETRAMETHOXY-2-BUTENE

The present invention relates to an improved process for the preparation of tetramethoxybutene by reacting 2,5-dimethoxydihydrofuran with methanol in the presence of solid catalysts having acidic centers.

Tetramethoxybutene is an important intermediate for preparing $C_{10}$-dialdehyde of the formula

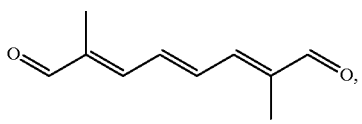

which in turn is a key building block for the synthesis of carotenoids such as β-carotene, astaxanthin and lycopene.

According to the process as described by C. M. Cox, D. A. Whiting, J. Chem. Soc. Perkin Trans. 1 1991, 1907–1911, V. M. Likhosherstov, Russ. J. Org. Chem. 1983, 19, 1176–1178, and S. M. Makin, N. I. Telefina, Z h. Obshch. Khim. 1962, 32, 1104–1109, and in U.S. Pat. No. 2,768,976 and DE 956 946, tetramethoxybutene is prepared from furan and bromine in methanol. Dimethoxydihydrofuran is formed in situ after 1,4-addition of bromine to the furan and subsequent nucleophilic substitution of the bromine by methanol. Owing to the formation of Br during the bromine substitution, the dimethoxydihydrofuran immediately reacts further to give tetramethoxybutene.

This process has serious disadvantages: the synthesis has to be conducted at temperatures of from −30 to −50° C., which is difficult to realize technically: the use of bromine requires a high expenditure on safety. Furthermore, bromine is an expensive reagent and highly corrosive, and it is necessary to equip the production plant with expensive specialty materials. In addition, the hydrogen bromide which is formed in equimolar amounts has to be neutralized during work up, producing large amounts of waste salts. It is in principle possible to conduct this synthesis using less expensive chlorine, but the disadvantages described for bromine remain, and the reaction is also significantly slower.

Since dimethoxydihydrofuran can advantageously be obtained by oxidation of furan in methanol, it has also been described to convert dimethoxydihydrofuran into tetramethoxybutene in the presence of a strong dissolved acid, e.g. p-toluenesulfonic acid or hydrogen chloride. Since this reaction which corresponds to the following reaction equation

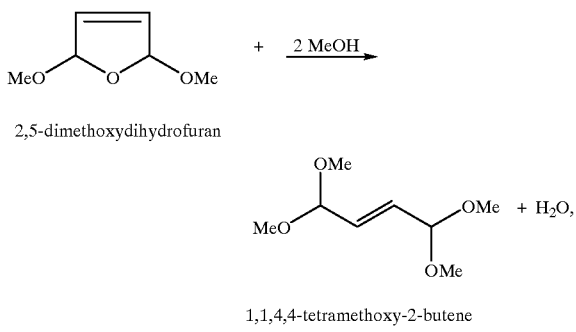

is a particular type of a transacetalization with formation of one mole of water, the water which is released must be removed from the equilibrium. According to the process of EP-A 0 581 097, this problem is solved by adding trimethyl orthoformiate, which is relatively expensive. Furthermore, it is not easy to transfer this process to the continuous scale. Here it is also necessary to neutralize the dissolved catalyst by the addition of a base to be able to stop the reaction at its optimum. Finally, N. Clauson-Kaas, J. T. Nielsen, E. Boss, Acta Chem. Scand. 1955, 9, 111–115, describe the use of aprotic Lewis acids, e.g. boron trifluoride, but the tetramethoxybutene yield was only 9% of theory.

Another problem of the prior art processes is the formation of considerable amounts of the byproduct pentamethoxybutane, reducing the tetramethoxybutene yield.

It is an object of the present invention to provide a process which allows the technically simple preparation of tetramethoxybutene, in particular in a continuous manner and in good yield, while reducing the formation of pentamethoxybutane.

We have found that this object is achieved by carrying out the reaction in the presence of solid catalysts having acidic centers. This results not only in high selectivities, in particular at partial conversion, but also in lower amounts of pentamethoxybutane byproduct. Unconverted dimethoxybutene can be returned to the reaction after distillation of the reaction products with removal of the water which has formed.

More specifically, the novel process relates to the preparation of 1,1,4,4-tetramethoxy-2-butene by reacting 2,5-dimethoxydihydrofuran with methanol in the presence of acids, which comprises carrying out the reaction in the presence of solid catalysts having acidic centers.

Solid catalysts having acidic centers are in particular acidic organic ion exchangers or inorganic oxidic catalysts which have acidic centers and are selected from the group consisting of zeolites in the H form, acidic mixed oxides and sheet silicates having acidic centers.

The catalysts to be used according to the invention essentially belong to four groups consisting of
 a) acidic organic ion exchangers which are preferred,
 b) zeolites in the H form,
 c) acidic mixed oxides, and
 d) sheet silicates having acidic centers.

a) Acidic Organic Ion Exchangers

Acidic organic ion exchangers are conventional, partially crosslinked chain polymers which are derived from styrene/divinylbenzene, in particular, and which contain preferably sulfonic acid groups, e.g. of the formula

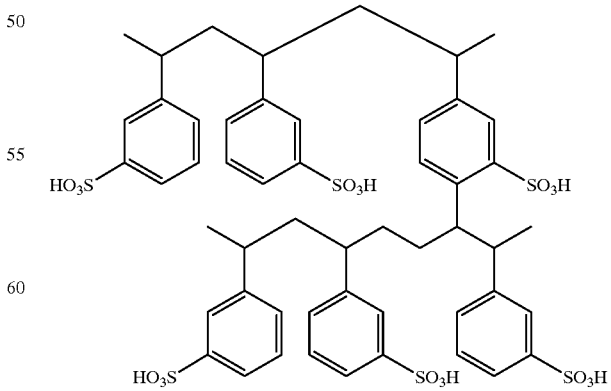

Ion exchangers of this type are commercially available, e.g. from DOW Chemical or BAYER Aktiengesellschaft.

Examples are Dowex® 50WX, Serdolit Red®, Amberlyst® 15, Lewatit® K2431, Navion® H$^L$, Amberlite® IR120, Duolite® C20, Lewatit® S100 and Lewatit® K2641.

b) Zeolites in the H Form

Preference is given to the acidic H form of 12-ring zeolites of the structure type BETA, Y, EMT and mordenite and 10-ring zeolites of the pentasil type. As well as the elements aluminum and silicon, zeolites can also contain boron, gallium, iron or titanium in their framework. Furthermore, they can also be partially exchanged with the elements of group IB, IIB, IIIB, IIIA or VIIIB and the lanthanide elements.

Zeolites to be used as catalysts include, for example, zeolites in the acidic H form of the structure type MFI, MEL, BOG, BEA, EMT; MOR, FAU, MTW, LTL, NES, CON or MCM-22 according to the structure classification given in W. M. Meier, D. H. Olson, C h. Baerlocher, Atlas of zeolite Structure Types, Elsevier, 4th ed., 1996.

Particular examples are the zeolites ZBM-20, Fe-H-ZSM5, Sn-beta zeolite, beta zeolite, Zr-beta zeolite, H-beta zeolite, H-mordenite, USY, Ce-V zeolite, H-Y zeolite, Ti/B-beta zeolite, B-beta zeolite or ZB-10.

c) Acidic Mixed Oxides

The acidic mixed oxides to be used according to the invention are in particular superacidic mixed oxides which have been described repeatedly in the literature. Reference may be made, for example, to R. J. Gillespie, Acc. Chem. Res. 1 (1968) 202 and R. J. Gillespie and T. E. Peel, Adv. Phys. Org. Chem. 9 (972) 1.

Specific superacidic metal oxides which can be used in the reaction of the invention are disclosed by Kazushi Arata in Applied Catalysis A: General 146 (1996) 3–32 for the reaction of butene and pentanes.

Exemplary sections of this reference which pertain to the preparation of the superacidic metal oxides are reproduced susequent to the examples. Additional information provided by Arata on the properties of the superacidic metal oxides, as well as sources referenced by Arata have been omitted.

Suitable sulfatized or phosphatized metal oxides (i) are in particular phosphatized or sulfatized zirconium oxide or titanium oxide which may include further elements such as iron, cobalt or manganese.

Preferred sulfatized or phosphatized catalysts are:

| | |
|---|---|
| $ZrO_2SO_4$ | (S content 0.5–4 mol %) |
| $ZrO_2P_2O_5$ | ($P_2O_5$ content 3–20 mol %) |
| $Fe_2O_3P_2O_5$ | ($P_2O_5$ content 3–20 mol %) |
| $Co/Mn/ZrO_2SO_4$ | (S content 0.5–4 mol %; Co/Mn content 0.1–5 mol %) |
| $Fe/Mn/ZrO_2SO_4$ | (S content 0.5–4 mol %; Fe/Mn content 0.1–5 mol %) |

Preference is given to superacidic mixed metal oxides of groups (i) and (ii) which contain zirconium, titanium, iron, tin or Cr(III) on the one hand and tungsten or molybdenum on the other.

Specific examples are $TiO_2WO_3$, $Fe_2O_3WO_3$, $ZrO_2MoO_3$, $ZrO_2WO_3$, $Cr_2O_3WO_3$, $WO_3TiO_2$, $TiO_2WO_3$ or $SnO_2WO3SiO2$, the molar ratio of the oxides of group (i) to group (ii) usually being from 70:30 to 90:10.

In accordance with one embodiment of the process, the catalyst comprises, as an essential constituent, mixed oxides having acidic centers, which oxides consist of a combination of (i) oxides of titanium, zirconium, hafnium, tin, iron or Cr(III), and (ii) oxides of vanadium, chronmium(VI), molybdenum, tungsten or scandium, or the mixed oxides are sulfatized or phosphatized oxides of group (i), and the mixed oxides have been calcined at from 459° C. to 800° C. after combining.

d) Sheet Silicates Having Acidic Centers

For the purposes of the invention, sheet silicates having acidic centers are those having Lewis and/or Brönsted centers. Therefore, they may be sheet silicates to which said Lewis acids have been applied or which have been treated with acids such as sulfuric acid. However, preference is given to sheet silicates which have negative layer charges neutralized by protons. In this case, the acidic centers of the sheet silicates are essentially Brönsted centers formed in the sheet silicates having excess negative charges by exchange of the metal ions for protons.

The sheet silicates to be used according to the invention are especially aluminum silicates; they belong to the clay minerals and are composed of $SiO_2$ tetrahedron and $Al_2O_3$ octahedron layers, part of the silicon in the tetrahedron layer being replaced by trivalent cations, preferably aluminum, and/or part of the aluminum in the octahedron layer being replaced by bivalent cations, preferably magnesium, so that negative layer charges result.

Sheet silicates having negative charges occur naturally as montmorillonites, vermiculites or hectorites or can be prepared synthetically.

A more detailed description is given in Z. M. Thomas and W. Z. Thomas, Principles and Practice of Heterogeneous-Catalysis, 1997, Vetc. ISBN 3-527-29239-8, p. 347 ff.

However, preference is given to naturally occurring montmorillonite which is converted into its H form by treatment with acids.

An example is montmorillonite of the formula

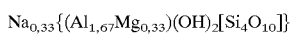

$Na_{0.33}\{(Al_{1.67}Mg_{0.33})(OH)_2[Si_4O_{10}]\}$ having layer charges from about 0.6 to 0.2 per formula unit.

To partially or completely neutralize the negative layer charges with protons, the exchangeable cations, usually alkali metal or alkaline earth metal ions, in the naturally occurring or synthetic sheet silicates are exchanged for protons. This is done in a conventional manner, e.g. by treatment with sulfuric acid or hydrochloric acid.

Since the sheet silicates containing protons instead of alkali metal or alkaline earth metal ions are thermally less stable, it is also possible to use pillared clays in which the layers are supported against one another. The preparation of such pillared clays is described in detail in Figuras, Catal. Rev. Sci. Eng. 30 (1988) 457 or Jones, Catal. Today (2 (1988) 357, which are incorporated here in the reference.

Specific examples of sheet silicates having negative layer charges which are neutralized by protons are: montmorillonite, vermiculite and hectorite.

The catalysts to be used according to the invention are employed in pulverulent or preferably particulate form, for example in the form of granules, extrudates or spheres.

The heterogeneous catalyst maintains its activity over a prolonged period of time. The inorganic catalysts can then be reactivated, for example by burning off in air at above 450° C. For these reasons the novel process is economically and environmentally particularly advantageous.

The reaction is either carried out batchwise, for example as a suspension process, or preferably over a fixed-bed catalyst, in a continuous flow reactor.

In the batchwise reaction, the catalyst is typically used in amounts of from 1 to 50, preferably from 5 to 30, % by weight, based on dimethoxydihydrofuran. Methanol is generally used in excess over the stoichiometrically required amount, for example in 2 to 40 times the molar amount, preferably in a molar excess of from 2 to 20, in particular from 1.5 to 10.

However, preference is given to the continuous process for which only a slight excess of methanol is required without substantially reducing the yield. It is therefore possible to carry out the reaction at a molar ratio of dimethoxydihydrofuran to methanol of 1:2–1:4, preferably 1:2.4–1:4.

The reaction according to the invention usually takes place at from −10 to 100° C., preferably from 0 to 40° C., in particular from 15 to 30° C., and at residence times of from 1 to 30 min, preferably from 10 to 60 min.

In the batchwise embodiment of the invention, dimethoxydihydrofuran is stirred together with an excess of methanol, e.g. in combination with an acidic ion exchanger, at e.g. 0–25° C. for several hours, the catalyst is filtered off and the reaction mixture is worked up by distillation. Unconverted dimethoxydihydrofuran can be reused.

However, it is advantageous to carry out the reaction in a continuous manner by passing dimethoxydihydrofuran together with methanol over a fixed-bed acidic catalyst. The reaction is advantageously carried out only to a partial conversion, e.g. less than 80% of theory. The mixture leaving the reactor is worked up by distillation and the unconverted dimethoxydihydrofuran and the dehydrated methanol are returned to the reaction.

Preferred reactors are tubular reactors in which the acidic catalyst is arranged in one or more beds.

EXAMPLES
(DMD=2,5-dimethoxydihydrofuran; TMB=1,1,4,4-tetramethoxy-2-butene; PMB=1,1,2,4,4-pentamethoxybutane)

Example 1

Dimethoxydihydrofuran (DMD 25.2 g, 0.19 mol) was added to a suspension of an acidic ion exchanger (29 g of Dowex®50WX4; DOW Corp.) in methanol (290 ml) at 0° C. while stirring slowly. After stirring at 0° C. for 14 h, the ion exchanger was filtered off. GC analysis of the methanol solution gave 55.7% of tetramethoxybutene (TMB), 42.0% of DMD and 2.0% of pentamethoxybutane (PMB) byproduct, corresponding to a conversion of 58% and a selectivity of 97%. This reaction was carried out at 10° C. and yielded, after a reaction time of 4 h, 57.3% of TMB, 39.4% of DMD and 2.9% of PMB, as determined by GC. This corresponds to a conversion of 61% and a selectivity of 95%.

Example 2

DMD (25.2 g, 0.19 mol) was added to a suspension of an acidic ion exchanger (29 g of Dowex®50WX4; (DOW Corp.) in methanol (290 ml) at 10° C. while stirring slowly. After stirring at 10° C. for 5 h, the ion exchanger was filtered off. GC analysis of the methanol solution gave 59.1% of TMB, 36.4% of DMD and 4.0% of PMB byproduct, corresponding to a conversion of 64% and a selectivity of 94%.

Example 3

DMD (8.70 g, 0.07 mol) was added to a suspension of an acidic ion exchanger (10 g of Lewatit K2641) in methanol (100 ml) at 25° C. while stirring slowly. After stirring at 25° C. for 2 h, the ion exchanger was filtered off. GC analysis of the methanol solution gave 53.2% of TMB, 41.2% of DMD and 4.4% of PMB byproduct, corresponding to a conversion of 59% and a selectivity of 92%.

Example 4

DMD (2.72 g, 0.02 mol) was added to a suspension of an acidic ion exchanger (10 g of Lewatit K2641) in methanol (100 ml) at 25° C. while stirring slowly. After stirring at 25° C. for 30 min, the ion exchanger was filtered off. GC analysis of the methanol solution gave 27.9% of TMB, 67.4% of DMD and 3.3% of PMB byproduct, corresponding to a conversion of 72% and a selectivity of 95%.

Example 5

Dimethoxydihydrofuran (DMD, 0.68 g, 0.005 mol) was added to a suspension of an acidic ion exchanger (10 g of Lewatit K2641, Bayer) in methanol (100 ml) at 25° C. while stirring slowly. After stirring at 25° C. for 15 min, the ion exchanger was filtered off. GC analysis of the methanol solution gave 34.6% of TMB, 63.1% of DMD and 1.5% of PMB byproduct, corresponding to a conversion of 65% and a selectivity of 98%.

Example 6

A solution of dimethoxydihydrofuran (110 g) in methanol (1000 g) was kept at 5° C. and pumped from below into a vertical glass column which was filled with Lewatit K2641 ion exchanger. The pump rate was chosen to result in a contact time of 10 h. The glass column was also kept at 0° C. The methanol solution leaving the top of the glass column was analyzed by GC: 54.8% of TMB, 41.1% of DMD, 3.2% of PMB, corresponding to a conversion of 59% and a selectivity of 94%. A residence time of 15 h yielded 58.8% of TMB, 34.5% of DMD, 5.6% of PMB, corresponding to a conversion of 66% and a selectivity of 91%.

Example 7

A solution of dimethoxydihydrofuran (110 g) in methanol (1000 g) was kept at 0° C. and pumped from below into a vertical glass column which was filled with Dowex® 50WX4 ion exchanger. The pump rate was chosen to result in a contact time of 3 h. The glass column was also kept at 0° C. The methanol solution leaving the top of the glass column was analyzed by GC: 54.9% of TMB, 40.9% of DMD, 3.7% of PMB, corresponding to a conversion of 60% and a selectivity of 1094%.

Example 8

For comparison: reaction using p-toluenesulfonic acid as catalyst p-Toluenesulfonic acid (1.9 g, 0.01 mol) was added to a solution of dimethoxydihydrofuran (37.0 g, 0.29 mol) in methanol (420 ml) at 25° C. and the mixture was stirred for 24 h. GC analysis gave 53.0% of TMB, 40.0% of DMD, 7.0% of PMB, corresponding to a conversion of 60% and a selectivity of 88%.

The following is a reproduction of exemplary sections of Kazushi Arata's publication in Applied Catalysis A: General 146 (1996) 3–32, which relate to the preparation of superacidic metal oxides. The page numbers indicated in braces correspond to the page numbers of Arata's publication; sources referenced by Arata have been omitted:

Sulfated Metal Oxides 2.1. Detailed Procedure for Preparation of $SO_4/Fe_2O_3$, $TiO_2$, $ZrO_2$ 2.1.1. Preparation of $Zr(OH)_4$ Two hundred grams of $ZrOCl_2.8H_2O$ are dissolved into 2.5 liter of distilled water, and ammonium hydroxide (28%) is added dropwise into the aqueous solution with stirring until the solution has a pH value of 8. Usually the solution at once suddenly solidified and then liquefied to colloidal state. The aqueous portion is decanted from the precipitates, and fresh water is added followed by stirring and again decanting the aqueous portion; washing of the precipitates by decantation is repeated until the total amount of water used is 60 liters, with almost no chloride ions being detected in the washing. The precipitates are dried at 100° C. for 24 h.

The hydroxide is prepared in the manner described above from $ZrO(NO_3)_2.2H_2O$ as a starting material. Since residual nitrate ions are thermally decomposed, thorough washing of the precipitates is not needed; a few times would be enough for the decantation washing, in this point the preparation being easier.

2.1.2. Preparation of $H_4TiO_4$

A 290-ml volume of $Ti[OCH(CH_3)_2]_4$ is added to 2 liter of distilled water with stirring, and the white precipitates formed are dissolved by gradually adding 250 cm$^3$ of conc. $HNO_3$ with stirring. Ammonium hydroxide (28%), ~300 cm$^3$, is added into the aqueous solution with stirring until pH 8 of the solution followed by allowing to stand for a day, washing the precipitates by decantation of the 5-1 beaker twice, filtering, and finally drying at 100° C. for 24 h.

Another batch of $H_4TiO_4$ is prepared by hydrolyzing $TiCl_4$ as follows. A volume of 80 cm$^3$ of $TiCl_4$ is gradually added to 2 l of distilled water in a 5-l beaker cooled by ice water, large amounts of HCl gas being formed. Ammonium hydroxide is added until pH 8 (at room temperature) followed by the above procedures; the precipitates are washed thoroughly by decantation using 60 liter of water until no chloride ions are detected in the filtrate. The aqueous portion might become cloudy during washing, but the white washing can be decanted.

2.1.3. Preparation of $Fe(OH)_3$ and Amorphous $Fe_2O_3$

Five hundred grams of $Fe(NO_3)_3.9H_2O$ are dissolved in 2 l of water in a 5-l beaker followed by hydrolyzing with ammonium hydroxide (~300 cm$^3$ used, pH 8), washing, and drying as above. The decantation washing is performed until the liquid portion becomes cloudy (7–8 times).

Amorphous $Fe_2O_3$ is prepared by thermally decomposing $Fe(NO_3)_3.9H_2O$ at around 200° C. or higher; brown fuming gas is generated by decomposition of iron nitrate after fusion of the nitrate, and solid iron oxides are obtained on heating for 3–6 h.

2.1.4. Sulfate Treatment, Calcination, and Catalytic Action

The above prepared materials are powdered below 100 mesh followed by pouring 30 cm$^3$ of aqueous sulfuric acid (0.5 M concentration for Ti and Zr materials, 0.25 M for Fe) onto 2 g of the dried hydroxides or oxides on a filter paper, and drying in air; the iron materials are again powdered because of solidification after drying.

After calcination of the sulfate-adsorbed materials in air, the substances are catalytically active for the skeletal isomerization of butane to isobutane at room temperature or even at 0° C. The activities are dependent on the calcination temperature; the maximum activity is observed with calcination at 575–650° C. for the $ZrO_2$ catalyst (SO4/$ZrO_2$), 525° C. for $SO_4$/$TiO_2$, and 500° C. for $SO_4$/$Fe_2O_3$.

The material prepared by hydrolyzing $FeCl_3$ with ammonia followed by treating with $H_2SO_4$ and calcining had a tendency to be converted into iron sulfate; the catalyst obtained by using 0.05 M $H_2SO_4$ showed activity higher than that using 0.25 M for the ethanol dehydration, and only the catalyst prepared by the treatment with 0.05 M showed activity for butane, while the catalyst prepared from $Fe(NO_3)_3$ was highest in activity when treated with 0.25 M $H_2SO_4$. The catalyst prepared from $FeCl_3$ and 0.5 M $H_2SO_4$ gave the XRD pattern to be a mixture of $\alpha$-$Fe_2O_3$ and $Fe_2(SO_4)_3$ forms, while the sample similarly prepared from $Fe(NO_3)_3$ gave only the oxide form without the sulfate one.

The catalysts can be also obtained by the treatment with ammonium sulfate, but the catalytic activity is usually lower than that with sulfuric acid. The catalyst is usually calcined in a Pyrex tube and sealed in an ampoule until use to exclude humidity. The appearance of the catalysts with the sulfate treatment differs greatly from that without the treatment. The former catalysts are finely powdered solids which coat the wall of a glass ampoule obscuring vision, whereas the latter is not. Coating the wall of the glass ampoule is, however, not the case when the sample has adsorbed moisture from the air. The catalysts obtained from isopropoxide of Ti and nitrates of Fe and Zr as starting materials are high in activity and easy to prepare.

For the heating method ammonium hydroxide (28%) was added dropwise to 25 g of $ZrOCl_2.8H_2O$ dissolved in 0.5 l of distilled hot water (50–60° C.), the final pH being made to vary from 5 to 9. The solution including the precipitates was kept in a water bath wormed at 50–60° C. for 2 h followed by washing the precipitates two times with 0.25 l of hot water for each and drying at 100° C.

2.2. Detailed Procedure for Preparation of $SO_4$/$SnO_2$, $SiO_2$, $Al_2O_3$ 2.2.1. $SO_4$/$SnO_2$ The $SnO_2$ catalyst with superacidity was synthesized by a preparation method different from the cases of $ZrO_2$, $TiO_2$, and $Fe_2O_3$.$Sn(OH)_4$ is obtained by hydrolyzing 100 g of $SnCl_4.xH_2O$ dissolved in 2 l of water with ammonium hydroxide (28%); final pH of the solution is adjusted to be 9.5–10 (the hydroxides being dissolved at pH values above 10). The precipitates are washed by decantation three to five times until their conversion into colloidal state and drying at 100° C. The hydroxides (2 g) are exposed to 30 cm$^3$ of 3 M $H_2SO_4$ (not <1 M) in a beaker for 30 min followed by filtering, drying, and calcining in air at 550° C., the maximum activity being observed with calcination at 550° C.

2.2.2. $SO_4$/$SiO_2$

Silica gel is obtained by hydrolyzing 100 cm$^3$ of $Si(OC_2H_5)_4$ with 100 cm$^3$ of water and a few drops of $HNO_3$. The mixture is stirred until the gel formation. The precipitates are obtained by evaporation of excess water and ethanol, formed by hydrolysis of $Si(OC_2H_5)_4$, followed by drying at 100° C., and powdering. The silica gel (3 g) is exposed to $SO_2Cl_2$ for 1 h followed by evacuating HCl evolved by the reaction of surface OH group with $SO_2Cl_2$ and excess $SO_2Cl_2$ in vacuum, and calcining in air at 400° C.

2.2.3. $SO_4$/$Al_2O_3$

In the case of the sulfate-treated superacids of Fe, Ti, Zr, Hf, Si and Sn, superacid sites are not created by the treatment of sulfate ion on the crystallized oxides but rather on the amorphous forms, followed by calcination to the crystallization. The superacid of $Al_2O_3$ is prepared from the crystallized oxide, $\gamma$-$Al_2O_3$; highly active catalysts are obtained by treatment on the crystallized oxide rather than the amorphous one. The most active catalyst is obtained by exposing $\gamma$-$Al_2O_3$ to 2.5 M $H_2SO_4$ followed by calcining in air at 550–65° C.

Appearance of the catalyst looks quite like those of $SO_4$/$TiO_2$ and $SO_4$/$ZrO_2$; the catalyst is a finely powdered solid that coats the wall of the glass ampoule.

2.3. Miscellaneous Catalysts

Hafnium is the third element in the same group as Ti and Zr in transition metals of the Periodic Table. The $SO_4$/$HfO_2$ catalyst was prepared in the same manner as $SO_4$/$ZrO_2$ from $HfCl_4$ as a starting material; the catalyst was active for the skeletal isomerization of butane, the maximum activity being observed with treatment with 1 M $H_2SO_4$ and calcination at 700° C.

A substance obtained by calcination of $Zr(SO_4)_2$ shows an acid strength of $-13.16 < H_0 \leq -12.70$ and activity for the reaction of pentane to be a superacid, the material being a mixture of crystallized zirconium oxide and sulfate form. The catalyst is prepared by heating $Zr(SO_4)_2 \cdot 4H_2O$ at 250° C. followed by powdering and calcination in air at 725° C. for 3 h.

3. Superacids by Metal Oxides

3.1. $WO_3/ZrO_2$ and $MoO_3/ZrO_2$

3.1.1. Detailed Procedure for the Preparation

Ten grams of $Zr(OH)_4$, obtained from $ZrOCl_2$, are impregnated with 3.8 g of aqueous ammonium metatungstate $[(NH_4)_6(H_2W_{12}O_{40}) \cdot nH_2O$, 50 wt % $WO_{13}]$ and 15 cm$^3$ of water in a 100 cm$^3$ beaker followed by evaporating water at room temperature, drying, and calcining in air at 600–900° C. The concentration is 15 wt. % W based on the hydroxide, 13 wt. % W after calcination at 650–950° C. The analogous superacid is also formed by the kneading method with tungstic acid ($H_2WO_4$) which is insoluble in water; a wet mixture of 10 g of $Zr(OH)_4$ and 2.04 g of $H_2WO_4$ with a little water is kneaded for 3 h.

The $WO_3/ZrO_2$ catalyst is white in color, $WO_3$ being highly dispersed into the $ZrO_2$ lattice. If the color does not disappear, it is advised that zirconia gel is heated at 300° C. before impregnation of the tungstate.

Ten grams of $Zr(OH)_4$ are impregnated with 2.54 g of molybdic acid ($H_2MoO_4$) dissolved in 2 cm$^3$ of ammonium hydroxide (28%) and 15 cm$^3$ of water followed by evaporating water at room temperature, drying, and calcining in air. The concentration is 5 wt. % Mo metal based on the hydroxide.

3.2. $WO_3/SnO_2$, $TiO_2$, $Fe_2O_3$ $Sn(OH)_4$, $H_4TiO_4$, and $Fe(OH)_3$ were obtained by hydrolyzing guaranteed grade reagents of $SnCl_4$, $TiCl_4$, and $Fe(NO_3)_3$, respectively, with ammonium hydroxide until pH 8 of the solution, washing, drying at 300° C., and powdering the precipitates (32–60 mesh), washing of the precipitates of $Sn(OH)_4$ being performed a few times by decantation. The hydroxides were impregnated with aqueous ammonium metatungstate $[(NH_4)_6(H_2W_{12}O_{40})]$ followed by evaporating water, drying, calcining in air for 3 h. The concentration was 15 wt % W based on the hydroxides (11–13 wt. % after calcination).

3.3. $B_2O_3/ZrO_2$

Zirconium hydroxide was impregnated with aqueous boric acid followed by evaporating water and calcining in air at 500–700° C. (3–7 wt % B). The same catalyst was obtained by suspending the hydroxide in 2-propanol solution of trimethyl borate followed by adding water to hydrolysis of the borate.

4. Metal-promoted Superacids

4.1. $SO_4/ZrO_2$ Promoted with Noble Metals

The $SO_4/ZrO_2$ matter is recently used by the addition of platinum for stabilizing the catalyst, being reduced before use in most cases; usually less than 1 wt % of Pt on the surface was effective in preventing catalyst deactivation under hydrogen pressure.

The catalyst was prepared as follows. Zirconia gel was impregnated with aqueous hydrogen hexachloroplatinate (IV) hexahydrate ($H_2PtCl_6 \cdot 6H_2O$) followed by evaporating water and drying at 100° C.; the concentration was 0.5–10 wt % Pt based on the hydroxide. The dried material was then kneaded well with ammonium sulfate; the quantity of $(NH_4)_2SO_4$ was 15 wt % (3.6 wt % S) based on the Pt—$ZrO_2$. The kneaded material was pre-heated in a beaker at 150° C. for 1.5 h followed by calcining at 600° C. for 3 h.

The chlorides of Ir, Pt(II), Rh, Ru, and Pd used are insoluble in water, and thus the catalysts with those materials were all prepared by the kneading method without the impregnation step; the metal concentration was equivalent to Pt of 7.5 wt % based on $Zr(OH)_4$ [$1.92 \times 10^{-3}$ mole of the metal chlorides to 5 g of $Zr(OH)_4$].

Preparation of the Pt-doped superacid is mainly classified into two general procedures; one is an incipient wetness technique by impregnation of zirconia gel with 0.5 M $H_2SO_4$ followed by a second impregnation with a solution of $H_2PtCl_6$. The second procedure is the opposite method, where the first impregnation of the gel is with the platinum matter followed by sulfation of the platinum-doped zirconia.

The sulfation was performed by the following five methods:

(1s) Exposure of samples (2 g) to 0.5 M $H_2SO_4$ (30 cm$^3$) on a filter paper followed by atmospheric dryness, (2s) Impregnation with 0.5 M $H_2SO_4$ (3.6 wt % S), (3s) Impregnation with an aqueous solution of ammonium sulfate (3.6 wt % S), (4s) Kneading with ammonium sulfate without water (15 wt % the sulfate, 3.6 wt % S), and (5s) The same procedures as (1s) using 0.5 M $(NH_4)_2SO_4$.

The loading of platinum was carried out by (1p) impregnation with aqueous $H_2PtCl_6 \cdot 6H_2O$ followed by evaporating residual water and drying at 100° C. or (2p) kneading with $PtCl_2$ in the same manner as (4s), the concentration being 7.5 wt % Pt based on the gel (8 wt % after calcination). All samples were finally calcined in a quartz crucible at 600° C. for 3 h.

4.2. $SO_4/ZrO_2$ Promoted with Iron and Manganese

Zirconia gel was impregnated with aqueous solution of $FeCl_3$, $MnCl_2 \cdot 4H_2O$, $CoCl_2 \cdot 6H_2O$, $NiCl_2 \cdot 6H_2O$, $(NH_4)_2CrO_4$, $(NH_4)_6Mo_7O_{24} \cdot 4H_2O$, $(NH_4)_6(H_2W_{12}O_{40}) \cdot nH_2O$, $SnCl_2 \cdot 2H_2O$, or $HfCl_4$ followed by evaporating water and drying at 100° C.; the concentration was equivalent to 2.1 wt % Fe (equivalent to 7.5 wt % Pt) based on the hydroxide [$1.92 \times 10^{-3}$ mole of the metal materials to 5 g of $Zr(OH)_4$]. The dried material was then kneaded well with ammonium sulfate (15 wt %) without water followed by calcining in air at 600° C. for 3 h.

4.3. Iron Supported Zirconia

A highly active superacid of 2 wt % Fe-supported $ZrO_2$ for the skeletal isomerization of butane to isobutane was obtained by exposing $Fe_2O_3/ZrO_2$ to 0.5 M $H_2SO_4$ followed by calcining in air at 700° C. for more than 24 h. $Fe_2O_3/ZrO_2$ was obtained by impregnating zirconia gel with an aqueous solution of $Fe(NO_3)_3$ followed by calcining at 300° C. for 3 h, the concentration being 2 wt % Fe based on the gel.

We claim:

1. A process for the preparation of 1,1,4,4-tetramethoxy-2-butene by reacting 2,5-dimethoxydihydrofuran with methanol, which comprises carrying out the reaction in the presence of a solid catalyst having acidic centers, which catalyst is an inorganic oxidic catalyst selected from the group consisting of zeolites in the H form, acidic mixed oxides and sheet silicates having acidic centers.

2. The process of claim 1, wherein the H form zeolite has a MFI, MEL, BOG, BEA, EMT, MOR, FAU, MTW, LTL, NES, CON or MCM 22 type structure.

3. The process of claim 1, wherein the H form zeolite is a 12-ring zeolite having a BETA, Y, EMT or mordenite type structure or is a 10-ring zeolite having a pentasil type structure.

4. The process of claim 1, wherein the catalyst comprises, as an essential constituent, mixed oxides having acidic centers, and said mixed oxides consist of a combination of
   (i) oxides of titanium, zirconium, hafnium, tin, iron or Cr(III), and
   (ii) oxides of vanadium, chronmium (VI), molybdenum, tungsten or scandium, or the mixed oxides are sulfatized or phosphatized oxides of group (i), and the mixed oxides have been calcined at from 459° C. to 800° C. after combining.

5. The process of claim 1, wherein the catalyst is a sheet silicate which is doped with a Lewis acid or a sheet silicate which has negative layer charges neutralized by protons.

6. The process of claim 1, wherein said 2,5-dimethoxydihydrofurane is continuously reacted with 2 to 40 times the molar amount of methanol at from −10 to 100° C.

7. The process of claim 6, wherein the reaction is carried out to a partial conversion of less than 80% of theory, excess methanol and the water which has formed are removed in a subsequent distillation, and unconverted dimethoxydihydrofuran is returned to the reaction.

* * * * *